United States Patent [19]

Andress, Jr.

[11] 4,144,180

[45] Mar. 13, 1979

[54] DERIVATIVES OF TRIAZOLE AS LOAD-CARRYING ADDITIVES FOR GEAR OILS

[75] Inventor: Harry J. Andress, Jr., Wenonah, N.J.

[73] Assignee: Mobil Oil Corporation, New York, N.Y.

[21] Appl. No.: 838,698

[22] Filed: Oct. 3, 1977

[51] Int. Cl.$^2$ .................. C10M 1/44; C10M 1/10; C07D 261/00; C07D 249/00
[52] U.S. Cl. ..................... 252/32.5; 252/49.9; 252/50; 252/51.5 A; 260/307 F; 260/308 B
[58] Field of Search ............ 252/32.5, 49.9, 50, 252/51.5 A; 260/308 B, 307 F

[56] References Cited

U.S. PATENT DOCUMENTS

| | | | |
|---|---|---|---|
| 3,969,237 | 7/1976 | Andress | 252/32.5 |
| 3,986,967 | 10/1976 | Okorodudu | 252/32.5 |
| 4,052,324 | 10/1977 | Braid | 252/32.5 |
| 4,070,294 | 1/1978 | Jones | 252/32.5 |

*Primary Examiner*—Delbert E. Gantz
*Assistant Examiner*—Irving Vaughn
*Attorney, Agent, or Firm*—Charles A. Huggett; Hastings S. Trigg

[57] ABSTRACT

Load-carrying properties of gear oils are increased by the addition of triazole derivatives obtained by reacting benzotriazole or an alkylbenzotriazole with alkylphosphates, alkylphosphonates, or primary fatty amines, a naphthenyl oxazoline, or an alkenylsuccinyl mono- or bis-oxazoline.

16 Claims, No Drawings

DERIVATIVES OF TRIAZOLE AS LOAD-CARRYING ADDITIVES FOR GEAR OILS

BACKGROUND OF THE INVENTION

1. Field of the Invention

This invention is directed to benzotriazole derivatives useful as load-carrying agents for gear oils.

2. Description of the Prior Art

In U.S. Pat. No. 3,969,237, there are described copper passivators that are reaction products of (A) benzotriazole and (B) a hydrocarbyl carboxylic acid having at least 18 carbon atoms, mono- and di-substituted phosphonates, or mono- and di-substituted phosphates wherein the organic substituents contain at least 15 carbon atoms; reacted in a mole ratio of (A) to (B) from about 1:1 to about 1:0.5. It is to be noted that the only organic substituents shown were nonylphenyl, i.e., alkylaromatic. There is no disclosure of amines and oxazolines.

On the other hand, in this application the phosphonates and phosphates are substituted with $C_4$-$C_{14}$ alkyl groups. Further, the mole ratio of (A) to (B) herein is 1:2.

DESCRIPTION OF THE INVENTION

This invention provides a lubricant composition comprising a major amount of an oil of lubricating viscosity or greases thereof and a load carrying amount of the reaction product of (A) benzotriazole or a lower alkylbenzotriazole with (B) a mono- or di-alkylphosphonate having 4 to 14 carbon atoms per alkyl group, a mono- or di-alkyl phosphate having 4 to 14 carbon atoms per alkyl group, a primary fatty amine having 6 to 26 carbon atoms, a naphthenyl oxazoline, or an alkenylsuccinyl mono- or bis-oxazoline; wherein the reaction is conducted at a temperature between about 100° C. and about 200° C. and in a mole ratio of (A) to (B) of 1:2, in the case of phosphonates and phosphates, and of about 1:1, in the case of amines and oxazolines.

It also provides said reaction products as new compositions of matter.

Description of Specific Embodiments

In preparing the reaction products of this invention, reactant (A) is benzotriazole (azimidobenzene) or a lower alkylbenzotriazole such as methylbenzotriazole (azimidotoluene).

Of the (B) reactants, the phosphonate reactant is a mono- or di-alkyl phosphonate, including mixtures, having 4 to 14 carbon atoms per alkyl group. Typical phosphonates include dibutyl phosphonate, dioctyl phosphonate, mixed mono- and di-tridecyl phosphonate, ditetradecyl catechol phosphonate, isodecyl phosphonate, and diisodecyl phosphonate. Dibutyl phosphonate $[(C_4H_9O)_2P(O)H]$ is particularly preferred.

The phosphate reactant is a mono- or di-alkyl phosphate, including mixtures, having 4 to 14 carbon atoms per alkyl group. Typical phosphates include dibutyl phosphate, tridecyl phosphate, ditridecyl phosphate, mixed mono- and di-tridecyl phosphate, tetradecyl phosphate and ditetradecyl phosphate.

The reaction between (A) the benzotriazole reactant and (B) the phosphonate reactant or the phosphate reactant is carried out at a temperature between about 100° C. and about 200° C. In this case, the mole ratio of (A) to (B) is 1:2.

The amine reactant is a primary fatty amine, preferably unsaturated, having 6 carbon atoms to 26 carbon atoms. Typical amines utilizable include oleylamine.

The oxazoline reactant is a naphthenyl oxazoline or an alkenylsuccinyl mono- or bis-oxazoline. The naphthenyl oxazoline is prepared by reacting equimolar amounts of naphthenic acid and tris-(hydroxymethyl) aminomethane. The alkenylsuccinyl bis-oxazoline is made by reacting one mole of an alkenylsuccinic acid having 10 carbon atoms to 50 carbon atoms per alkenyl group with one or 2 moles of tris-(hydroxymethyl)aminomethane. The reactions are carried out at a temperature between about 200° C. and about 250° C., preferably using an aromatic hydrocarbon, such as benzene or toluene, to remove water by azeotropic distillation through a water take-off trap, e.g., a Dean-Stark trap.

The reaction between (A) the benzotriazole reactant and (B) the amine reactant or the oxazoline reactant is also carried out at a temperature between about 100° C. and about 200° C. In this case the mole ratio of (A) to (B) is about 1:1.

The present invention contemplates lubricant compositions which contain a small amount sufficient to improve load carrying properties of the aforementioned additives. Generally, for most applications, the additive is present in an amount from about 0.1 to about 5%, by weight, and preferably in an amount from about 0.1 to about 1%, by weight. The lubricant compositions contemplated in accordance with the present invention may comprise any materials that normally exhibit insufficient antiwear properties. A field of specific applicability is the improvement of liquid hydrocarbon oils boiling within the range from about 75° F. to about 1000° F. Lubricant oils, improved in accordance with the present invention, may be of any suitable lubricating viscosity range from about 45 SSU at 100° F. to about 6000 SSU at 100° F. and, preferably, from about 50 to 250 SSU at 210° F. These oils having viscosity indexes from about 70 to about 95 are preferred. The average molecular weights of these oils may range from about 250 to about 800. In general, the lubricant may comprise any mineral or synthetic oil of lubricating viscosity.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

As hereinbefore indicated, the aforementioned additives may be incorporated as antiwear agents in grease compositions. Such oils can also include hydraulic oils, if so desired. When high temperature stability is not a requirement of the finished grease, mineral oils having a viscosity of at least 40 SSU at 150° F., and particularly those falling within the range from about 60 SSU to about 6000 SSU at 100° F. may be employed. The lubricating vehicles of the improved greases of the present invention, containing the above-described additives, are combined with a grease-forming quantity of a thickening agent. For this purpose, a wide variety of materials dispersed in the lubricating vehicle in grease-forming quantities in such degree as to impart to the resulting grease composition the desired consistency. Examplary of the thickening agents that may be employed in the grease formulation are non-soap thickeners, such as surface-modified clays and silicas, aryl ureas calcium complexes and similar materials. In general, grease thickeners may be employed which do not melt and dissolve when used at the required temperature within a particular environment; however, in all other respects, any material which is normally employed for thickening or gelling hydrocarbon fluids or forming greases can be used in preparing the aforementioned improved greases in accordance with the present invention.

EXAMPLE 1

A mixture of 36.4 grams (1.31 mols) of oleylamine and 125 grams (1.05 mols) benzotriazole was stirred at 140° C. for about three hours to form the final product.

EXAMPLE 2

A mixture of 388 grams (2.0 mols) dibutyl phosphonate and 133 grams (1.0 mol) tolyl triazole was stirred at 140° C. for about two hours to form the final product.

EXAMPLE 3

A mixture of 210 grams (0.4 mol) ditetradecyl catechol phosphonate and 26.6 grams (0.2 mol) tolyl triazole was stirred at 140 to 145° C. for about three hours to form the final product.

EXAMPLE 4

A mixture of 295 grams (0.8 mol) of a 50-50 mix of mono- and di-tridecyl phosphates and 54 grams (0.4 mol) tolyl triazole was stirred at 140° C. for about two hours to give the final product.

EXAMPLE 5

A mixture of 362 grams (1 mol) of diisodecyl phosphonate and 67 grams (0.5 mol) tolyl triazole was stirred at 140° C. for three hours to give the final product.

EXAMPLE 6

A mixture of 300 grams (1.0 mol) naphthenic acid and 121 grams (1.0 mol) tris-hydroxymethylamino) methane was refluxed in the presence of toluene diluent at about 215° C. until evolution of water ceased. To this compound (a naphthenyl oxazoline) was added 133 grams (1.0 mol) tolyl triazole and the mixture stirred for four hours at about 140° C. to give the final product.

EXAMPLE 7

A mixture of 185 grams (0.5 mol) iso octadecenyl succinic acid and 121 grams (1.0 mol) tris-(hydroxymethylamino) methane was refluxed in toluene at a temperature of about 250° C. until evolution of water ceased. The product is an isooctadecenylsuccinyl bis oxazoline.

EXAMPLE 8

A mixture of 269 grams (0.5 mol) of iso octadecenyl succinyl bis oxazoline (made according to Example 7) and 66.5 grams (0.5 mol) tolyl triazole was stirred at about 140° C. for six hours to form the final product.

The composition was tested in the Timken Load Test. This test is a known test used to determine the load carrying properties of additives in lubricating oil compositions. The test is conducted by placing a steel test cup on a shaft which can be rotated at 800 r.p.m. Just below the cup and in contact with it is a small stationary steel block. A load is placed on these parts by means of a lever arm which pushes the block upwards against the rotating cup, which acts as a roller bearing, while the lubricant flows between the two surfaces. The load is gradually increased at 10-minute intervals until failure occurs. Failure is determined by visual inspection during the running period.

Timken OK Load Test

Additives blended in a conventionally refined mineral oil containing a sulfurized hydrocarbon, metal passivator, pour point depressant, antioxidant, demulsifier, antirust agent, and defoamant.

| Additive | | Conc. % | Load in lbs. |
|---|---|---|---|
| Base oil blend | | 0 | 50 |
| " | + Example 1 | 0.1 | 60 |
| " | + Example 2 | 0.1 | 65 |
| " | + Example 3 | 0.1 | 60 |
| " | + Example 4 | 0.1 | 60 |
| " | + Example 5 | 0.1 | 60 |
| " | + Example 6 | 0.1 | 65 |
| " | + Example 8 | 0.1 | 60 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A lubricant composition comprising a major amount of an oil of lubricating viscosity or greases thereof and a load carrying amount of the reaction product of (A) benzotriazole or a lower alkylbenzotriazole with (B) a mono- or di-alkylphosphonate having 4 to 14 carbon atoms per alkyl group, a mono- or di-alkyl phosphate having 4 to 14 carbon atoms per alkyl group, a primary fatty amine having 6 to 26 carbon atoms, a naphthenyl oxazoline, or an alkenylsuccinyl mono- or bis-oxazoline; wherein the reaction is conducted at a temperature between about 100° C. and about 200° C. and in a mole ratio of (A) to (B) of 1:2, in the case of phosphonates and phosphates, and of about 1:1, in the case of amines and oxazolines.

2. A composition of claim 1, wherein (A) is benzotriazole, (B) is oleylamine, and the mole ratio of (A) to (B) is about 1:1.

3. A composition of claim 1, wherein (A) is tolyl triazole, (B) is dibutyl phosphonate, and the mole ratio of (A) to (B) is about 1:2.

4. A composition of claim 1, wherein (A) is tolyl triazole, (B) is ditetradecyl catechol phosphonate, and the mole ratio of (A) to (B) is about 1:2.

5. A composition of claim 1, wherein (A) is tolyl triazole, (B) is a 50—50 mixture of mono- and di-tridecyl phosphates, and the mole ratio of (A) to (B) is about 1:2.

6. A composition of claim 1, wherein (A) is tolyl triazole, (B) is diisodecyl phosphonate, and the mole ratio of (A) to (B) is about 1:2.

7. A composition of claim 1, wherein (A) is tolyl triazole, (B) is a naphthenyl oxazoline, and the mole ratio of (A) to (B) is about 1:1.

8. A composition of claim 1, wherein (A) is tolyl triazole, (B) is isooctadecenyl succinyl bis-oxazoline, and the mole ratio of (A) to (B) is about 1:1.

9. The reaction product of (A) benzotriazole or a lower alkylbenzotriazole with (B) a mono- or di-alkylphosphonate having 4 to 14 carbon atoms per alkyl group, a mono- or di-alkyl phosphate having 4 to 14 carbon atoms per alkyl group, a primary fatty amine having 6 to 26 carbon atoms, a naphthenyl oxazoline, or an alkenylsuccinyl mono- or bis-oxazoline; wherein the reaction is conducted at a temperature between about 100° C. and about 200° C. and in a mole ratio of (A) to (B) of about 1:2, in the case of phosphonates and phosphates, and of about 1:1, in the case of amines and oxazolines.

10. A reaction product of claim 9, wherein (A) is benzotriazole, (B) is oleylamine, and the mole ratio of (A) to (B) is about 1:1.

11. A reaction product of claim 9, wherein (A) is tolyl triazole, (B) is dibutyl phosphonate, and the mole ratio of (A) to (B) is about 1:2.

12. A reaction product of claim 9, wherein (A) is tolyl triazole, (B) is ditetradecyl catechol phosphonate, and the mole ratio of (A) to (B) is about 1:2.

13. A reaction product of claim 9, wherein (A) is tolyl triazole, (B) is a 50-50 mixture of mono- and di-tridecyl phosphates, and the mole ratio of (A) to (B) is about 1:2.

14. A reaction product of claim 9, wherein (A) is tolyl triazole, (B) is diisodecyl phosphonate, and the mole ratio of (A) to (B) is about 1:2.

15. A reaction product of claim 9, wherein (A) is tolyl triazole, (B) is a naphthenyl oxazoline, and the mole ratio of (A) to (B) is about 1:1.

16. A reaction product of claim 9, wherein (A) is tolyl triazole, (B) is isooctadecenyl succinyl bis-oxazoline, and the mole ratio of (A) to (B) is about 1:1.

* * * * *

UNITED STATES PATENT AND TRADEMARK OFFICE
CERTIFICATE OF CORRECTION

PATENT NO. : 4,144,180
DATED : March 13, 1979
INVENTOR(S) : HARRY J. ANDRESS, JR.

It is certified that error appears in the above-identified patent and that said Letters Patent are hereby corrected as shown below:

TITLE OF INVENTION: "TRIAZOLE" should be --TRIAZOLES--

Column 3   Line #5    "Examplary" should be

--Exemplary--

Signed and Sealed this

Nineteenth Day of June 1979

[SEAL]

Attest:

RUTH C. MASON
Attesting Officer

DONALD W. BANNER
Commissioner of Patents and Trademarks